(12) United States Patent
Grifols Lucas et al.

(10) Patent No.: US 10,624,924 B2
(45) Date of Patent: Apr. 21, 2020

(54) METHOD AND DEVICE FOR TREATING BLOOD CHOLESTEROL DISORDERS

(75) Inventors: Victor Grifols Lucas, Barcelona (ES); Victor Grifols Roura, Barcelona (ES)

(73) Assignee: GRIFOLS, S.A., Barcelona (ES)

( * ) Notice: Subject to any disclaimer, the term of this patent is extended or adjusted under 35 U.S.C. 154(b) by 0 days.

(21) Appl. No.: 13/418,123

(22) Filed: Mar. 12, 2012

(65) Prior Publication Data

US 2013/0236559 A1 Sep. 12, 2013

(51) Int. Cl.
*A61K 35/14* (2015.01)
*A61M 1/34* (2006.01)
*A61K 35/16* (2015.01)

(52) U.S. Cl.
CPC ......... *A61K 35/14* (2013.01); *A61M 1/3496* (2013.01); *A61K 35/16* (2013.01)

(58) Field of Classification Search
CPC ............................. A61K 35/14; A61M 1/3496
USPC ........................................................ 604/5.03
See application file for complete search history.

(56) References Cited

U.S. PATENT DOCUMENTS

| | | | |
|---|---|---|---|
| 4,350,156 A | 9/1982 | Malchesky | |
| 4,374,731 A | 2/1983 | Brown | |
| 4,540,401 A * | 9/1985 | Marten | 604/28 |
| 4,657,529 A | 4/1987 | Prince | |
| 5,258,149 A | 11/1993 | Parham et al. | |
| 5,846,427 A | 12/1998 | Kessler et al. | |
| 5,919,902 A * | 7/1999 | Becker et al. | 530/350 |
| 6,248,238 B1 | 6/2001 | Burtin | |
| 6,423,022 B1 | 7/2002 | Roeher | |
| 6,551,266 B1 * | 4/2003 | Davis, Jr. | 604/6.09 |
| 6,627,151 B1 | 9/2003 | Borberg | |
| 7,402,246 B2 | 7/2008 | Bomberger | |
| 8,048,015 B2 * | 11/2011 | Bellotti et al. | 604/5.03 |
| 8,268,787 B2 | 9/2012 | Bellotti et al. | |
| 8,480,607 B2 | 7/2013 | Davies | |
| 2003/0127390 A1 | 7/2003 | Davis, Jr. | |
| 2003/0232712 A1 * | 12/2003 | Dolecek | A61M 1/3693 494/37 |
| 2004/0102732 A1 | 5/2004 | Naghavi et al. | |
| 2004/0153023 A1 | 8/2004 | Borberg et al. | |
| 2005/0051497 A1 | 3/2005 | Latino | |

(Continued)

FOREIGN PATENT DOCUMENTS

| CN | 100998898 A | 7/2007 |
|---|---|---|
| CN | 101076364 A | 11/2007 |

(Continued)

OTHER PUBLICATIONS

Parker et al., Proc. Natl. Acad. Sci. USA, vol. 83, pp. 777-781.*

(Continued)

*Primary Examiner* — Ariana Zimbouski
(74) *Attorney, Agent, or Firm* — Dinsmore & Shohl LLP

(57) ABSTRACT

A method and device for treating cholesterol disorders includes administering at least one treatment regime including two or more rounds of plasmapheresis to a patient having abnormal total cholesterol, abnormal LDL levels and/or abnormal HDL levels prior to treatment. Treatment according to the method results in decreased LDL levels in patients having abnormal LDL levels and increased HDL levels in patients having abnormal HDL levels. Each subsequent round of plasmapheresis is conducted weekly, but no more than twice per week.

20 Claims, 14 Drawing Sheets

(56) References Cited

U.S. PATENT DOCUMENTS

| | | | |
|---|---|---|---|
| 2007/0181499 | A1 | 8/2007 | Roberts |
| 2010/0038317 | A1 | 2/2010 | Bissler |
| 2010/0105990 | A1 | 4/2010 | Bene |
| 2010/0160361 | A1 | 6/2010 | Hislop et al. |
| 2010/0192686 | A1 | 8/2010 | Kamen |
| 2010/0316730 | A1* | 12/2010 | Latino et al. ............ 424/613 |
| 2011/0142700 | A1 | 6/2011 | Gura |
| 2012/0165685 | A1 | 6/2012 | Weasler et al. |
| 2013/0046225 | A1 | 2/2013 | Nose |
| 2013/0202601 | A1 | 8/2013 | Fornoni |
| 2013/0236559 | A1 | 9/2013 | Grifols Lucas |

FOREIGN PATENT DOCUMENTS

| | | |
|---|---|---|
| CN | 201006071 Y | 1/2008 |
| EP | 570232 A2 | 11/1993 |
| RU | 2113240 C1 | 6/1998 |
| RU | 2195321 C2 | 12/2002 |
| RU | 2310478 C1 | 11/2007 |
| WO | 86000231 | 1/1986 |
| WO | 9637602 A1 | 11/1996 |
| WO | 2004056318 A8 | 6/2006 |
| WO | 2011015380 | 2/2011 |
| WO | 2011080191 | 7/2011 |
| WO | 2012109282 | 8/2012 |

OTHER PUBLICATIONS

Maaskant et al., Removal of Low Density Lipoprotein from Blood Plasma using Cross-linked, Sulfated Polyvinylalcohol (1986).*

B.Braun website, http://www.bbraun.com/cps/rde/xchg/bbraun-com/hs.xsl/apheresis-01.html, Wayback version (2009).*

Saal et al. (Removal of low-density lipoproteins in patients by extracorporeal immunoadsorption, The American Journal of Medicine 1986;80(4):583-9).*

Stoffel et al. (Application of Specific Extracorporeal Removal of Low Density Lipoprotein in Familial Hypercholesterolaemia, The Lancet—Nov. 7, 1981;318(8254), 1005-1007).*

Thompson et al. (A systematic review of LDL apheresis in the treatment of cardiovascular disease, Atherosclerosis 2006;189:31-38).*

Title 21—Food and Drugs, Part 640—Additional Standards for Human Blood and Blood Products—Subpart G—Source Plasma; 21 CFR 640.60-640.76 (http://www.gpo.gov/fdsys/granule/CFR-2010-title21-vol7/CFR-2010-title21-vol7-sec640-61, accessed Oct. 14, 2015).*

Rose Raymond (Selling your body?: Plasma donation: examining a growing trend, http://archive.voxmagazine.com/stories/2009/06/17/selling-your-body/, accessed Oct. 14, 2015, published Jun. 17, 2009).*

Wayback Machine, https://web.archive.org/web/*/http://www.inova.org/upload/docs/Get%20Involved/Blood%20Donor/ibds-factsheets.pdf, Accessed May 25, 2016.*

Inova Blood Donor Services , http://www.inova.org/upload/docs/Get%20Involved/Blood%20Donor/ibds-factsheets.pdf, Saved Dec. 27, 2010.*

Donating Blood and Cholesterol [Archive] Straight Dope Message Board (http://boards.straightdope.com/sdmb/archive/index.php/t221021.html, Nov. 2, 2003, accessed May 25, 2016).*

ATP III Final Report: Appendix III—A Distributions of Total Cholesterol, LDL Cholesterol, HDL Cholesterol, and Triglycerides in the U.S. Adult Population, NHANES III Data (1988-1994) (Serum) (http://circ.ahajournals.org/content/106/25/3237/tab-figures-data, accessed Oct. 5, 2016k, published Dec. 17, 2002).*

Atsma et al. (Cardiovascular and demographic characteristics in whole blood and plasma donors: results from the Donor InSight study, Transfusion, Feb. 2011;51(2):412-20).*

Understanding Your Cholesterol Level, emedicinehealth, http://www.emedicinehealth.com/understanding_your_cholesterol_level/page2_em.htm, captured Mar. 7, 2011, accessed Jan. 27, 2017.*

Making Sense of Cholesterol Tests (Harvard Health Publishing, https://www.health.harvard.edu/heart-health/making-sense-of-cholesterol-tests, accessed Oct. 2, 2017).*

Detection, Evaluation, and Treatment of High Blood Cholesterol in Adults (Adult Treatment Panel III), Sep. 2002.*

Peffer et al. (Turbid plasma donations in whole blood donors: fat change?, Transfusion, Jun. 2011;51:1179-1187).*

Thomas et al., Plasma exchange in the management of homozygous familial hypercholesterolaemia, Lancet (LOS), 1, 1208-1211 (1975).*

Bechtloff, S., Tran-My, B., Haubelt, H., et al: A prospective trial on the safety of long-tem intensive plasmapheresis in donors. Vox Sanguinis. 2005; 88: 189-195.

Beigel, R., Beigel, Y.: Homozygous familial hypercholesterolemia: Long term clinical course and plasma exchange therapy for two individual patients and review of the literature. Journal of Clinical Apheresis. 2009; 24:219-224.

Bell, K., Kirby, Adrienne, K, Hayen, A., et al: Monitoring adherence to drug treatment by using change in cholesterol concentration: secondary analysis of trial data. British Medical Journal. 2011; 342:d12.

Bookstein, L., Gidding, S., Donovan, M., Smith, F: Day-to-day variability of serum cholesterol, triglyceride, and high-density lipoprotein cholesterol levels. Archives of Internal Medicine. 1990; 150: 1653-1657.

Burnouf, T., Kappelsberger, C., Frank, Kerstin, Burkhardt, T: Protein composition and activation markers in plasma collected by three apheresis procedures. Transfusion. 2003; 43:1223-1229.

Cohen, M., Oberman, H: Safety and long-term effects of plasmapheresis. Transfusion. 1970; 10: 58-66.

Dechmann-Sultemeyer, T., Linkeschova, R, Lenzen, K, Kuril, Z., et al: Tandem plasmapheresis and haemodialysis as a safe procedure in 82 patients with immune-mediated disease. Nephrology Dialysis Transplantation. 2009; 24:252-257.

Eason, S., Goudar, S., Centilli, J., Sayers, M: Experience with routine total nonfasting blood cholesterol screening of volunteer blood and component donors. Transfusion. 2011; 51: 731-736.

Edgren, G., Reilly, M., Hjalgrim, H., Nam Tran, T., et al: Donation frequency, iron loss, and risk of cancer among blood donors. Journal National Cancer Institute. 2008; 100:572-579.

Evans, K.: Low-density lipoprotein apheresis in patients with severe familial hypercholesterolemia refractory to, or intolerant of, lipid-lowering drug therapy: preventing the onset or progression of cardiovascular disease. Capstone project and theses dissertation. School of Physician Assistants, Pacific University. 2011.

Glaszlou, P., Irwig, L., Heritier, S., Simes, J., Tonkin, A.: Monitoring cholesterol levels: measurement error or true change? Annals of Internal Medicine. 2008; 148:656-661.

Irwig, L., Glasziou, P., Wilson, A: Estimating an individual's true cholesterol level and response to intervention. JAMA. 1991; 266: 1678-1685.

Ito, M., McGowan, M., Moriarty, P.: Management of familial hypercholesterolemias in adult patients: recommendations from the national lipid association expert panel on familial hypercholesterolemia. Journal of Clinical Lipidology. 2011; 5: S38-S45.

Makino, H., Harada-Shiba, M.: Long-term effect of low-density lipoprotein apheresis in patients with homozygous familial hypercholesterolemia. Therapeutic apheresis and dialysis. 2003; 7(4): 397-401.

Nazir, D., Roberts, R., Hill, S., McQueen, M.: Monthly intra-individual variation in lipids over a 1-year period in 22 normal subjects. Clinical Biochemistry. 1999: 32(5): 381-389.

Parhofer, K., Barrett, P., Demant, T., Richter, W. Schwandt, P.: Effects of weekly LDL-apheresis on metabolic parameters of apolipoprotein B in heterozygous familial hypercholesterolemia. Journal of lipid research. 1996; 37:2383-2393.

Schulzki, T., Seidel, H., Storch, H., et al: A prospective multicentre study on the safety of long-term intensive plasmapheresis in donors (SIPLA). Vox Sanguinis. 2006; 1-12.

Smart, N., Marshall, B., Daley, M., et al: Low-fat diets for acquired hypercholesterolemia. The Cochrane Collaboration. 2011; 2: 1-21.

Stefanutti, C., D'Alessandri, G., Russi, G., et al: Treatment of symptomatic HyperLp(a) lipoproteinemia with LDL-apheresis: a multicentre study. Atherosclerosis Supplements. 2009; 10: 89-94.

(56) References Cited

OTHER PUBLICATIONS

Szczepiorkowski, Z., Bandarenko, N., Kim, H., et al: Guidelines on the use of therapeutic apheresis in clinical practice—evidence-based approach from the apheresis applications committee of the American society for apheresis. Journal of Clinical Apheresis. 2007; 22:106-175.
Takahashi, K., Kobayashi, J., Bujo, H., et al: Long-term (14 years) effect of LDL apheresis on obstructive changes in aortocoronary saphenous-vein bypass graft in a case of heterozygous familial hypercholesterolemia with the LDL receptor proline to leucine mutation. Internal Medicine. 2000; 39(10): 804-809.
Tenenbaum, A., Fisman, E., Motro, M., Adler, Y.: Atherogenic dyslipidemia in metabolic syndrome and type 2 diabetes: therapeutic options beyond statins. Cardiovascular Diabetology. 2006; 5: 1-8.
Tran-Mi, B., Starch, H., Seidel, K., et al: The impact of different intensities of regular donor plasmapheresis on humoral and cellular immunity, red cell and iron metabolism, and cardiovascular risk markers. Vox Sanguinis. 2004; 86:189-197.
Vella, A., Pineda, A., O'Brien, T.: Low-density lipoprotein apheresis for the treatment of refractory hyperlipidemia. Mayo Clinic Proceedings. 2001; 76: 1039-1046.
Yokoyama, S., Hayashi, R., Satani, M., Yamamoto, A.: Selective Removal of low density lipoprotein by plasmapheresis in familial hypercholesterolemia. Arteriosclerosis. 1985; 5(6) 613-622.
Ananchenko, VG., et al., "Plasmapheresis in the treatment of patients with hypertension," 1991, pp. 20-22, vol. 10, Sovereign Medical (abstract only).
Brown, C.W., et al., "Model for a one-step plasma treatment device: Feasibility of cholesterol removal," Nov./Dec. 1997, pp. 884-889, vol. 43, No. 6, ASAIO Journal.
Chang, W.D., et al., "An implementation of a WSN-based medical monitoring system: A pilot study of the blood pressure monitoring of hemodialysis patients," 2012, pp. 83-89, vol. 5, No. 3, Engineering in Agriculture, Environment and Food (abstract only).
Girard, A., et al., "Effects of plasmapheresis on short-term variability of blood pressure in healthy donors," Oct. 1992, pp. 299-302, vol. 2, No. 5, Clinical Autonomic Research (abstract only).
Mineshima, M., et al., "Continuous monitoring of blood volume in double filtration plasmapheresis," Sep./Oct. 1998, pp. M465-M469, vol. 44, No. 5, ASAIO Journal.
Tello, R., "Continuous noninvasive blood pressure monitoring during hemodialysis," 1984, p. 81, Association for Advancement of Medical Instrumentation, Proceedings—AAMI 19th Annual Meeting: Abstracts on the application of technology to health care (abstract only).
Carretero and Oparil, Circulation, 101:329-35 (2000).
Glasson, Schweiz Med Wochenschr., 113(5):189-91 (1983) (abstract only).
Halperin et al., Hypertension, 47:45-50 (2006).
Heidland and Schaefer, New Perspectives in Hemodialysis, Peritoneal Dialysis, Arteriovenous Hemofiltration, and Plasmapheresis, 79-91 (1989).
Office Action in U.S. Appl. No. 14/727,403 issued by USPTO dated Jan. 20, 2017.
Waksman, A First-in-Man, Randomized, Placebo-Controlled Study to Evaluate the Safety and Feasibility of Autologous Delipidated High-Density Lipoprotein Plasma Infusions in Patients With Acute Coronary Syndrome, Journal of the American College of Cardiology, vol. 55, No. 24, Jun. 15, 2010.
Medical Advisory Secretariat, "Low density lipoprotein apheresis: an evidence-based analysis", Ontario Health Technology Assessment Series, 7(5), 2007.
Hemphill, Familial Hypercholesterolemia: Current treatment options and patient selection for low-density lipoprotein apheresis, 2010, 4, 346-349, Journal of Clinical Lipidology.
Extended European Search Report dated Jul. 8, 2013 for EP 13157889.0, pp. 1-8.
Expert Report mailed Oct. 28, 2015 for CL Application No. 2013-00667, pp. 1-9.
Office Action dated Dec. 9, 2015 for CN Application No. 201310078574.6, pp. 1-16.
Official Action dated Aug. 29, 2016 for RU Application No. 2013110503, pp. 1-8.
Official Action dated Dec. 27, 2016 for RU Application No. 2013110503, pp. 1-7.
Requirement dated Jun. 23, 2016 for MX/a/2013/002681, pp. 1-3.
Search Report dated Jan. 27, 2016 for TW Application No. 102108168, pp. 1-11.
Examination Search Report dated Jul. 18, 2017 for CA Application No. 2,809,012, pp. 1-8.
Rejection dated Apr. 26, 2017 for JP Application No. 2013-048810, pp. 1-4.
Examination Report dated Aug. 30, 2019 for Indian Application No. 702/DEL/2013, pp. 1-5.

\* cited by examiner

METHOD AND DEVICE FOR TREATING BLOOD CHOLESTEROL DISORDERS

BACKGROUND

The present invention refers to a method and a device for the removal of total cholesterol, low density lipoprotein cholesterol (LDL) and/or high density lipoprotein cholesterol (HDL) from whole blood. In particular, the device comprises means for separating blood plasma from red blood cells from said whole blood.

Plasmapheresis is a common medical procedure whereby plasma is separated from whole blood. It has been used to treat patients suffering from various chronic illnesses involving an exchange of volume of 2.5 L or more. Taking into consideration the large volume, when using plasmapheresis to treat medical conditions once the plasma is separated from the whole blood, the blood can be returned to the body with replacement fluids, such as fresh plasma and/or an albumin solution. Plasmapheresis has also been used for the purpose of obtain human plasma donations. In these cases, the volume extracted is no larger than 880 mLs, and the blood can be returned with or without replacement fluids.

When treating patients with therapeutic plasmapheresis, a catheter is placed in a large vein, such as in the arm, and a second catheter is placed in another vein, such as a vein in the foot or hand. Blood then passes out of the body via the catheter and through a separator. Plasma is separated from the whole blood. The blood without plasma the desired fluids and optional replacement fluids can be returned to the body via the second catheter. For plasma donations, however, automated plasmapheresis equipment is used where a single venipuncture is required, as the blood is removed and returned through the same site.

There are several different types of therapeutic plasmapheresis including: (i) plasma exchange in which plasma that is separated and discarded is replaced with fresh plasma or an albumin solution, (ii) double filtration plasmapheresis in which plasma is passed through a separator with a small pore size so as to selectively remove large molecular weight proteins, or (iii) plasma adsorption in which plasma flows into a plasma adsorption column wherein certain substances can be adsorbed and removed. Plasmapheresis used for plasma donations, however, uses mostly centrifugation (e.g., Haemonetics blood processing systems) or centrifugation with a simple filter (e.g, Fenwal blood processing systems).

It is known to use low-density lipoprotein therapeutic apheresis to treat patients suffering from familial hypercholesterolemia. Evans, Katie D., "Low-Density Lipoprotein Apheresis in Patients with Severe Familial Hypercholesterolemia Refractory to, or Intolerant of, Lipid-Lowering Drug Therapy: Preventing the Onset or Progression of Cardiovascular Disease" (2011). *School of Physician Assistant Studies*. Paper 268. Such studies have used low-density lipoprotein (LDL) apheresis as an adjunct to lipid-lowering drugs, and the apheresis is administered once every one to three weeks. Id at 10. However, reduction in LDL levels is typically accompanied by reduction in high-density lipoprotein (HDL) levels to varying degrees. Id at 9. Such an effect can be undesirable particularly in patients having borderline and/or low HDL levels.

As discussed in Yokoyama, S. et al., "Selective Removal of Low Density Lipoprotein by Plasmaphereis in Familial Hypercholesterolemia", (1985). *Artheriosclerosis* Vol. 5, No. 6, pp. 613-622. Therapeutic plasmaphereis was performed on patients using hollow-fiber membrane filters or selective adsorption of very low density lipoproteins to selectively remove LDL. Id. at 613. It was determined that membrane-filter plasma separators are not suitable for hyperchylomicronemic patients. Id a 616. While LDL levels were reduced, there was no statistically significant change in HDL levels and slight over-recoveries of HDL was attributed to reconcentration of the plasma. Id at 619.

A treatment regime in which periodic plasmapheresis, requiring smaller volumes than traditional therapeutic plasmapheresis, shorter duration time and a single venipuncture that reduces LDL levels in patients having abnormal LDL levels and/or increases HDL levels in patients having abnormal HDL levels would be desirable.

SUMMARY OF SELECTED FEATURES

A method of treating patients suffering from cholesterol disorders includes administering a first treatment regime comprising two or more rounds of plasmapheresis to a patient having abnormal total cholesterol levels, abnormal LDL levels and/or abnormal HDL levels when measured prior to treatment. The method decreases LDL levels in patients having abnormal LDL levels and increases HDL levels in patients having abnormal HDL levels. The subsequent round of plasmapheresis could be conducted about 2 to about 14 days after a previous round of plasmapheresis. For example, a first round occurring on day 1 could be followed up by a second round on day 4, the third round on day 8, and the fourth round could be on day 11.

DETAILED DESCRIPTION

Figure 1:
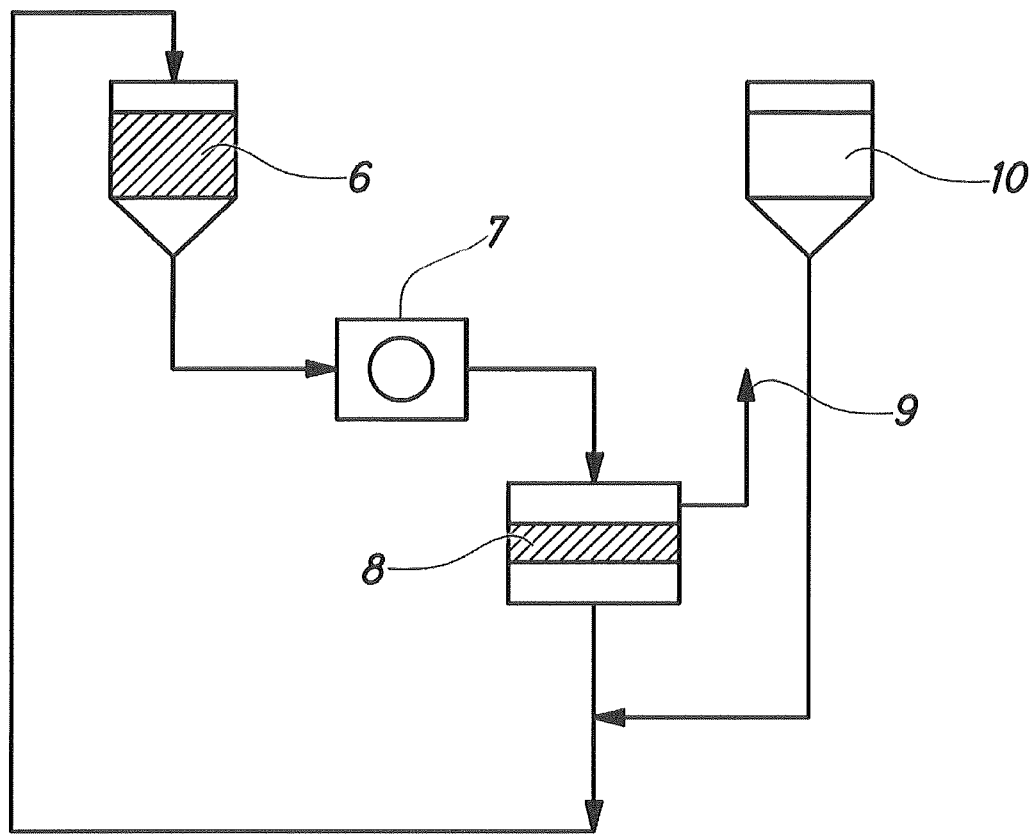
FIG. 1 is a device to be used in the method of the present invention.
Figure 2:
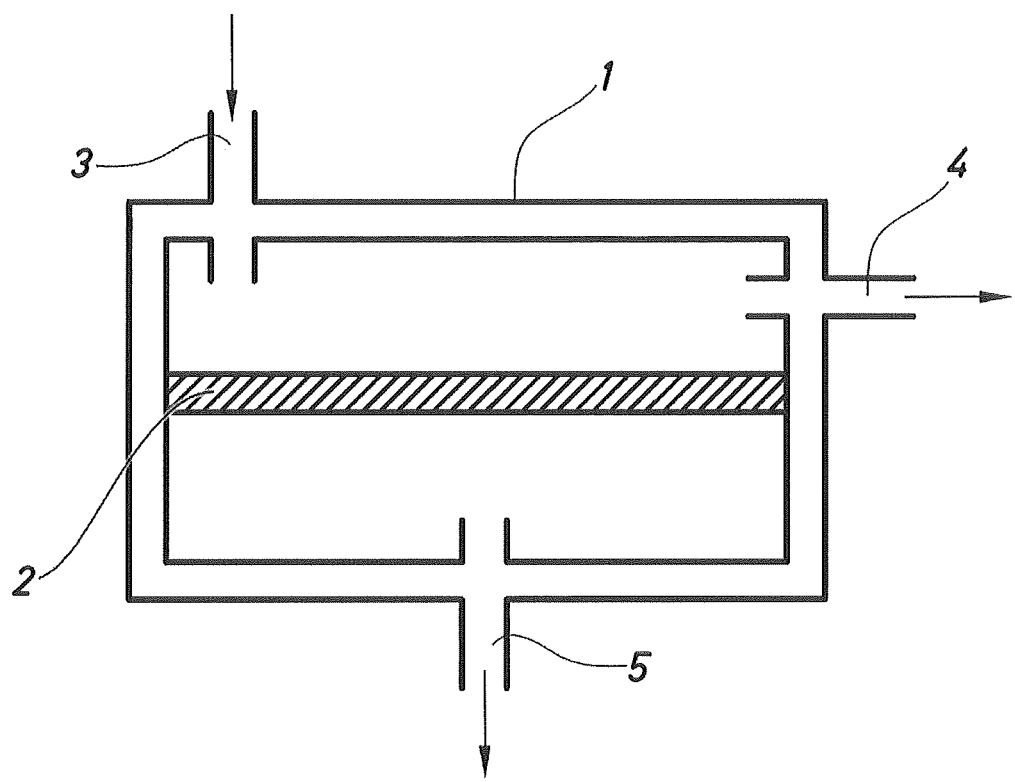
FIG. 2 is a diagram illustrating the separation process from whole blood.

A device for the removal of low density lipoprotein cholesterol (LDL) from whole blood is shown in FIG. 2. The device may comprise a housing (1), an entrance port (3) for receiving the whole blood from a donor, means for separating plasma from the cellular components of the blood (2), and a means for returning the cellular components of the blood to the a first exit port (4) from where the blood cellular components exit the device and a second exit port (5) from where the plasma exits the device. Preferably, said means for separating plasma from the cellular components of the blood are centrifugation means (i.e., a centrifuge). More preferably, said means for separating plasma from the cellular components of the blood are filtration means (i.e., a filter such as that used in double filtration plasmapheresis). The device of the present invention can be used in an extracorporeal method for reducing cholesterol as described herein. FIG. 1 is a schematic representation of the extracorporeal separation of plasma and red blood cells from whole blood. Whole blood is contained in a blood container (6) and is forced through the separation device (8) optionally by a pump (7). The plasma is then separated from red blood cells exiting the device via plasma exit port (9). The red blood cells are optionally sent to the whole blood container (6) and, optionally, along with a saline solution (10) added after exiting the device as necessary.

A method of treating hypercholesterolemia and other blood cholesterol disorders is provided herein. The method includes administering a first treatment regime comprising a first round of plasmapheresis to a patient having abnormal HDL and/or abnormal LDL levels. Additional rounds of plasmapheresis would be done to maintain an improved level of LDL or HDL. Plasmapheresis could be done twice a week, preferably with at least 2 days between sessions and less frequent plasmapheresis would be acceptable up to 10 days between treatments. The first treatment regime can be followed up by a second or more treatment regimes also comprising two or more rounds of plasmapheresis as described herein. The method can be used to reduce LDL levels in patients having abnormal LDL levels and/or to increase HDL levels in patients having abnormal HDL levels.

As used herein, the term "cholesterol disorders" denotes disorders in which the total cholesterol, LDL, and HDL levels are abnormal and includes disorders such as hypercholesterolemia, hyperlipidemia, dyslipidemia, and/or any other disorder in which abnormal total, LDL and/or HDL cholesterol levels are symptoms thereof.

As used herein, the term "hypercholesteroleinia" denotes a cholesterol disorder in which the levels of cholesterol in the blood are higher than normal as defined by the American Heart Association.

As used herein, the term "hyperlipidemia" denotes a disorder of lipid metabolism which results in abnormally high levels of cholesterol, triglycerides and lipoproteins in blood.

As used herein, the term "dyslipidemia" denotes a disorder in which a patient experiences an increase in LDL and a decrease in HDL levels.

As used herein, the term "high total cholesterol" denotes total cholesterol levels of greater than or equal to 240 milligram per deciliter (mg/dL) as defined by the American Heart Association (AHA) and National Heart, Lung, and Blood Institute (NHLBI).

As used herein, the term "borderline total cholesterol" denotes a total cholesterol level ranging from about 200 mg/dL to about 239 mg/dL as defined by the American Heart Association.

As used herein, the term "low-volume plasmapheresis" denotes plasmapheresis treatments involving blood volumes of about 1000 mL, preferably 800 mL or less.

As used herein, the term "abnormal LDL levels" denotes LDL levels that are high (i.e., greater than about 160 mg/dL as defined by the American Heart Association) or higher than desired (i.e., ranging from about 130 to about 159 mg/dL as defined by the American Heart Association).

As used herein, the term "abnormal HDL levels" denotes HDL levels that are low (i.e., less than about 40 mg/dL for males or less than about 50 mg/dL as defined by the American Heart Association) or borderline (i.e., about 40 mg/dL to about 60 mg/dL for males or about 50 mg/dL to about 60 mg/dL for females).

In a preferred embodiment, the method of treating cholesterol disorders includes administering a first treatment regime comprising two or more rounds of plasmapheresis to a patient having abnormal LDL levels and/or abnormal HDL levels prior to the first treatment regime. Preferably, the first treatment regime decreases LDL levels in patients having abnormal LDL levels and increases HDL levels in patients having abnormal HDL levels.

Preferably, each subsequent round of the first treatment regime is conducted about 5 to 7 days after a previous round of the first treatment regime. Alternatively, subsequent rounds of the first treatment regime is conducted twice a week, with preferably at least 2 days between donations.

The method can also include additional treatment regimes, each comprising two or more rounds of plasmapheresis spaced about 2 to about 14 days apart, (e.g., about 2 to about 10 days, about 4 to about 8 days, or about 5 to about 7 days). The additional treatment regimes can begin at any time.

In one embodiment, the method can also include combine with regular pharmacological therapy with statins to the patient before, during and/or after the first treatment regime in an amount sufficient to maintain and/or reduce total cholesterol and/or LDL levels. Suitable statins include those such as LIPITOR® manufactured by Pfizer, Inc.

Preferably, each round of the first and/or subsequent treatment regimes comprises a low-volume plasmaphereis in which less than about 1000 mL of blood is treated (e.g., less than about 800 mL or less than about 600 mL).

Preferably, the first and/or subsequent treatment regimes reduce LDL levels in patients having abnormal LDL levels prior to the first treatment regime by at least about 5 mg/dL to about 45 mg/dL, (e.g., about 10 mg/dL to about 35 mg/dL, about 15 mg/dL to about 30 dL, or about 20 mg/dL to about 25 mg/dL).

Also preferably, the first and/or subsequent treatment regimes increase HDL levels in patients having abnormal HDL levels prior to the first treatment regime by about 1 mg/dL to about 5 mg/dL or about 2 mg/dL to about 4 mg/dL.

In the preferred embodiment, each treatment regime last for at least about 2 weeks (e.g, at least about 4 weeks, at least about 6 weeks, about least about 8 weeks, at least about 10 weeks, at least about 12 weeks, at least about 14 weeks, at least about 16 weeks, at least about 18 weeks, at least about 20 weeks, at least about 22 weeks or more).

Also preferably, the method can include tailoring the first treatment regime and/or subsequent treatment regimes based on the total cholesterol, LDL, and/or HDL levels of the patient. Thus, the treatment regimes can be adjusted to vary the time between rounds, time between treatment regimes, use of statins, addition of diet or exercise, type of plasmapheresis, plasmapheresis volume and other such variables depending on the patient, how the patient reacts and/or adjust to treatment and the like. Moreover, each treatment regime can last for the same or different period of time than the first treatment regime.

Unexpectedly, it was found that the method described herein utilizing low-volume plasmapheresis and including two or more rounds of plasmapheresis with about 2 to about 14 days between sessions reduces LDL levels in patients having abnormal LDL levels and increases HDL levels in patients having abnormal HDL levels. These unexpected results are detailed below, and the results also serve as evidence that plasmapheresis does not pose a safety risk, only lowers LDL levels of patients having abnormal LDL levels, only raises HDL levels of patients having abnormal HDL levels and shows that these effects are only found when plasmapheresis is periodic rather than a singular event.

To evaluate the effects of plasmapheresis on the blood cholesterol levels of plasma donors, a study was conducted on a variety of patients having abnormal and normal cholesterol levels. The study was performed at nine collection centers in the United States and donors were studied for 16 weeks.

The protocol specified that participants donate at least once per week during the 16 week period. Under US guidelines, donations can be made up to 32 times during a 16 week period, however, the donation patterns varied so as to study the effect of different time periods between donations for patients having both abnormal and normal total cholesterol, LDL, and HDL levels.

Initially, non-fasting blood samples were collected prior to each donation and each sample was analyzed to determine the total cholesterol, HDL level, and LDL level. Donors also completed a short questionnaire on lifestyle factors that could affect cholesterol levels and whether or not they have started lipid-lowering treatment.

The study included 663 donors making a total of 9,153 donations over the course of the study. All study participants were first-time donors or previous donors who had not donated for at least six months prior to the initiation of the study.

The study included both male and female donors ranging in age from 18 years to 69 years old, who were qualified to donate plasma. Table 1 lists the number of donors by gender, race, age and weight and the percent of each group of the total.

TABLE 1

| | | Number of Donors | Percent (%) |
|---|---|---|---|
| Gender | Male | 407 | 61.4 |
| | Female | 256 | 38.6 |
| Race | Caucasian | 304 | 45.9 |
| | Hispanic | 119 | 17.9 |
| | African-American | 88 | 13.3 |
| | Not available | 152 | 22.9 |
| Age (years) | 18-24 | 263 | 39.7 |
| | 25-34 | 218 | 32.9 |
| | 35-44 | 103 | 15.5 |
| | ≥45 | 79 | 11.9 |
| Weight (lb) | <200 | 427 | 64.4 |
| | 200-249 | 164 | 24.7 |

TABLE 1-continued

| | Number of Donors | Percent (%) |
|---|---|---|
| 250-299 | 49 | 7.4 |
| ≥300 | 23 | 3.5 |

Table 2 shows the total cholesterol level, LDL level, HDL level and total study donations of the donors involved in the study.

TABLE 2

| | Group | Number of Donors | Percent (%) |
|---|---|---|---|
| Total Cholesterol* (mg/dL) | High (≥240) | 38 | 5.7 |
| | Higher than desired (200-239) | 132 | 19.9 |
| | Acceptable (<200) | 493 | 74.4 |
| LDL* (mg/dL) | High (≥160) | 41 | 6.2 |
| | Higher than desired (130-159) | 112 | 16.9 |
| | Acceptable (<130) | 510 | 76.9 |
| HDL* (mg/dL) | Low (<40, males; <50, females) | 228 | 34.4 |
| | Average (40-60, males; 50-60, females) | 341 | 51.4 |
| | Optimal (>60) | 94 | 14.2 |
| Total Study Donations | 2-10 | 296 | 44.6 |
| | 11-20 | 168 | 25.3 |
| | 21-32 | 199 | 30.0 |

*AHA/NHLBI-NCEP classification

The total number of donations was investigated as a relevant variable during the study.

It was believed that an analysis limited to considering the overall change for the complete study population could miss interim changes resulting from specific variables such as number of observations, days between donations, baseline cholesterol levels and others. Thus, a statistical model was needed that: (a) used information from individuals and their donations; (b) controlled for unequal contributions of each person; (c) allowed for the estimation of the independent contribution of each variable; and (d) accounted for the repeated measure among subjects and different number of observations.

A multivariable repeated measures regression model using the General Estimating Equation (GEE) approach was used to analyze the data. Using the GEE approach, the data set was used to construct a model to estimate the effect of plasmapheresis on cholesterol levels in donors with varying baseline cholesterol levels. This model takes into account that cholesterol measures for a given person are likely to be similar and accounts for varying number of follow up visits. Moreover, the model allows for analysis of measurements taken at different time intervals within and between donors. This model was interpreted similar to a multivariable regression model and allowed for the testing of the effect of each independent variable while controlling for the effects of other variables. Potential variables of interest included gender, age, weight, race, baseline total cholesterol, LDL, and HDL, time between donations, number of donations, and lifestyle changes, such as diet and exercise.

All variables of interest were evaluated using the model to determine which variable had significant effects. The final model employed baseline cholesterol level (3 groups), days between donations (3 groups), and gender (2 groups), which resulted in 18 different combinations (3×3×2).

It was determined that donor age, race, weight, and number of prior donations had little effect on cholesterol change. Moreover, responses on the lifestyle questionnaire did not show an independent effect on cholesterol change. The validity of the model was checked by comparing the estimated results of the GEE model to those actually observed in the dataset.

Figure 3:
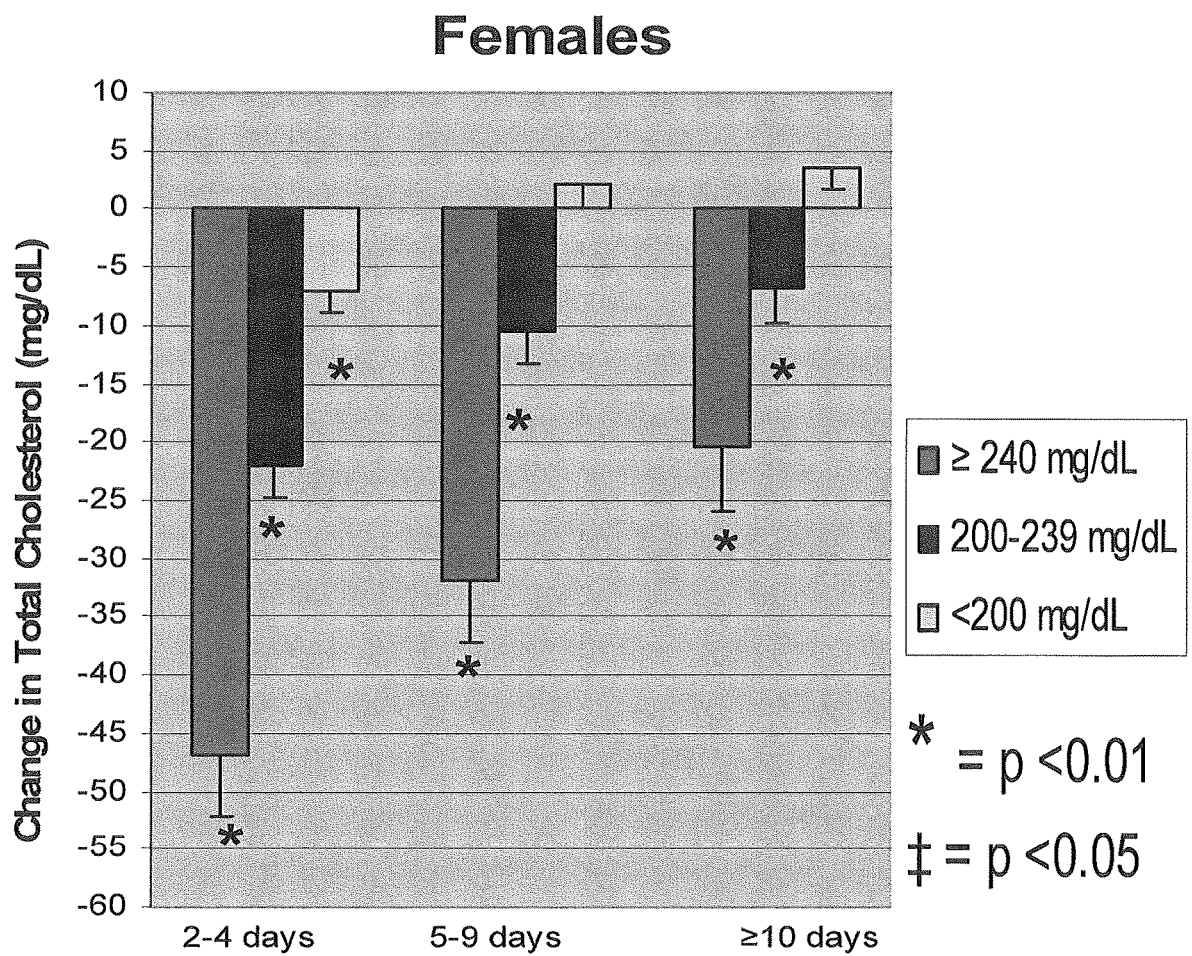
FIG. 3 is a graph illustrating the effect of plasmapheresis on total cholesterol (mg/dL) in female donors.
Figure 4:
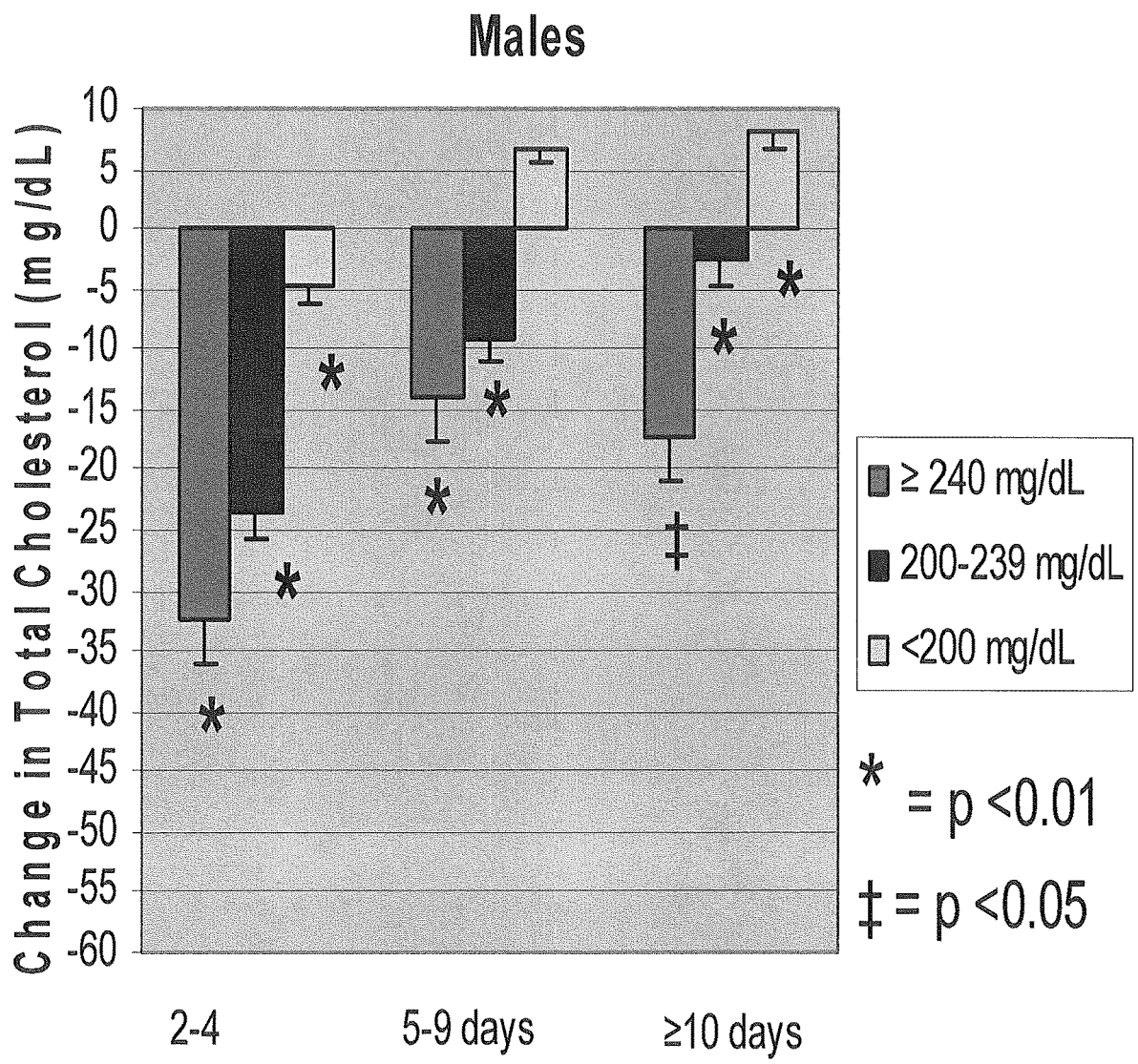
FIG. 4 is a graph illustrating the effect of plasmapheresis on total cholesterol (mg/dL) in male donors.

The effect of plasmapheresis on total cholesterol levels in female and male donors is shown in FIGS. 3 and 4. As shown in FIG. 3, female donors having abnormal cholesterol levels experienced a reduction in total cholesterol ranging from about 5 mg/dL to about 50 mg/dL over the course of the study. Female donors undergoing plasmapheresis with 2 to 4 days between sessions and having abnormal total cholesterol levels experienced the greatest reduction, ranging from about 20 mg/dL to about 50 mg/dL while those undergoing plasmapheresis with 5 to 9 days between sessions experienced reductions of about 10 mg/dL to about 35 mg/dL and those undergoing plasmapheresis after 10 or more days from the previous plasmapheresis saw a reduction of about 5 mg/dL to about 25 mg/dL.

As shown in FIG. 4, male donors having abnormal cholesterol levels experienced a reduction in total cholesterol ranging from about 1 mg/dL to about 35 mg/dL over the course of the study. Male donors undergoing plasmapheresis after 2 to 4 days from the previous plasmapheresis session and having abnormal total cholesterol levels experienced the greatest reduction, ranging from about 20 mg/dL to about 35 mg/dL while those undergoing plasmapheresis with 5 to 9 days between sessions experienced reductions of about 8 mg/dL to about 15 mg/dL and those undergoing plasmapheresis after 10 or more days from the last plasmapheresis session saw a reduction of about 1 mg/dL to about 20 mg/dL.

Figure 5:
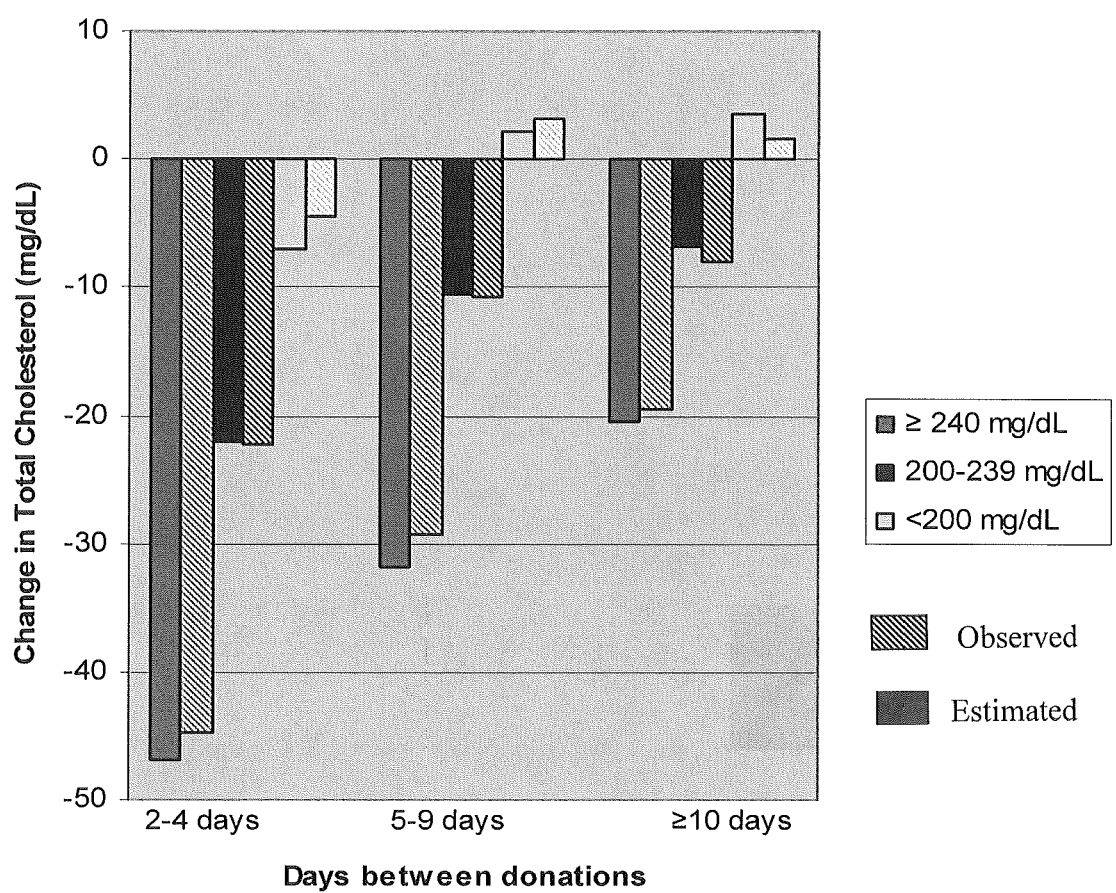
FIG. 5 is a graph illustrating the change from baseline, both estimated and observed, in total cholesterol for female donors.
Figure 6:
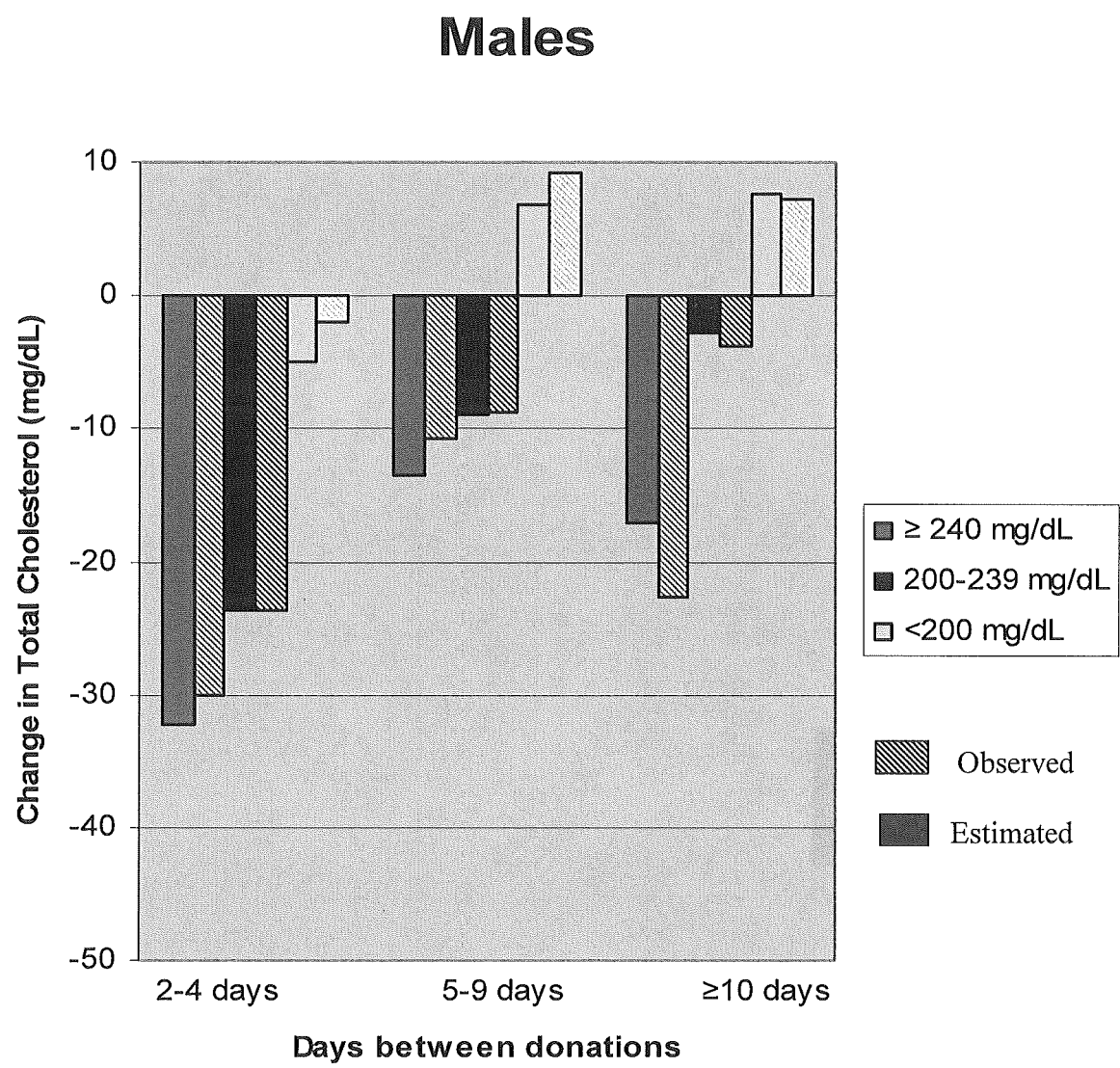
FIG. 6 is a graph illustrating the change from baseline, both estimated and observed, in total cholesterol for male donors.

FIGS. 5 and 6 illustrate the change from baseline in total cholesterol and compare study observations with GEE Model estimates. As shown in FIG. 5, females having high total cholesterol levels (i.e., greater than 240 mg/dL) experienced reductions slightly less than those that were estimated while females having borderline total cholesterol levels (i.e., about 200 mg/dL to about 239 mg/dL) experienced slightly greater reductions than those estimated by the GEE model.

As shown in FIG. 6, males having high total cholesterol levels (i.e., greater than 240 mg/dL) experienced reductions slightly less than those that were estimated for all periods except where greater than 10 days passed between rounds. Males having borderline total cholesterol levels (i.e., about 200 mg/dL to about 239 mg/dL) experienced cholesterol levels that were substantially the same as those estimated by the GEE model except where greater than 10 days passed between rounds of plasmapheresis. In that case, the observed reductions were slightly greater than estimated.

Figure 7:
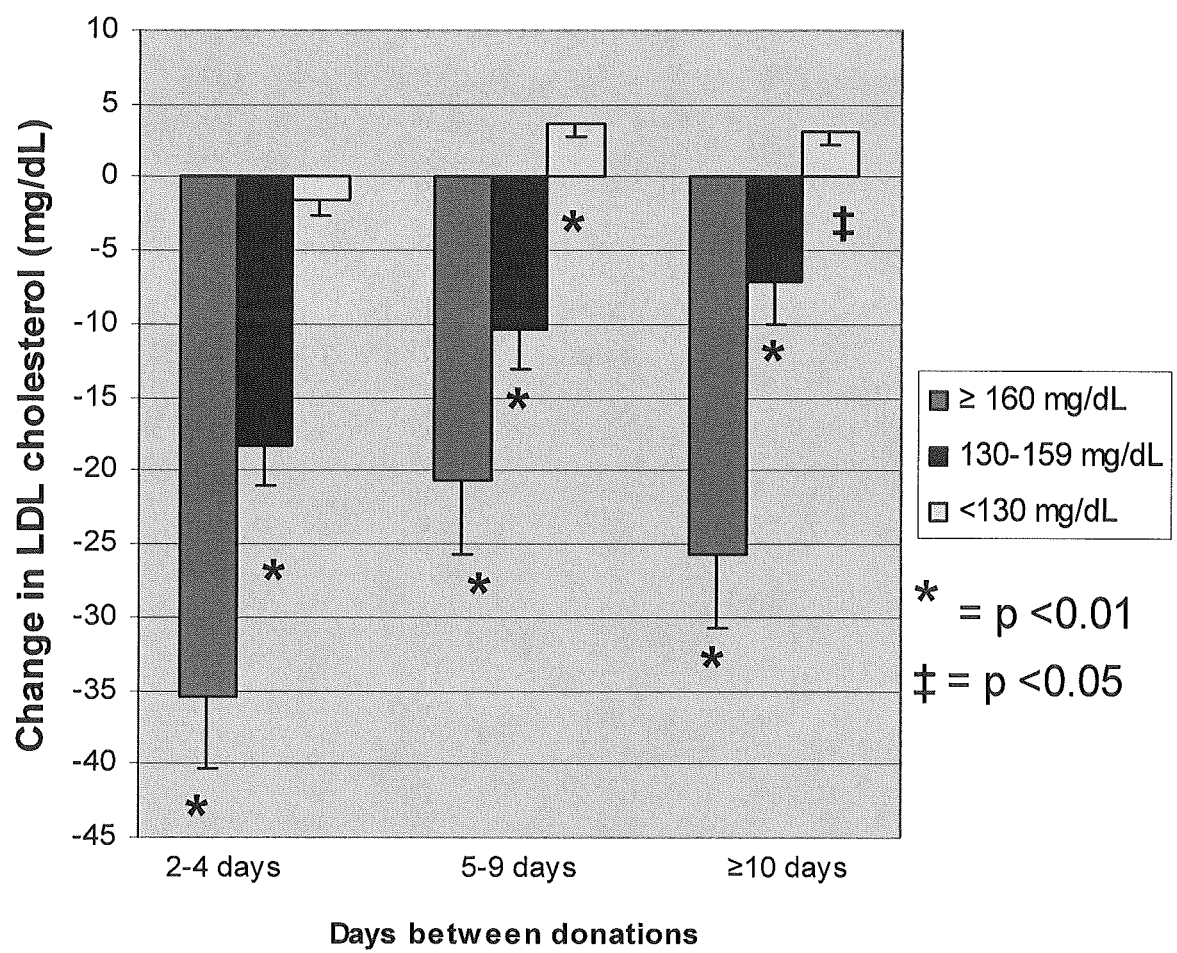
FIG. 7 is a graph illustrating the change in LDL cholesterol based on the number of days between plasmapheresis treatments for female donors.
Figure 8:
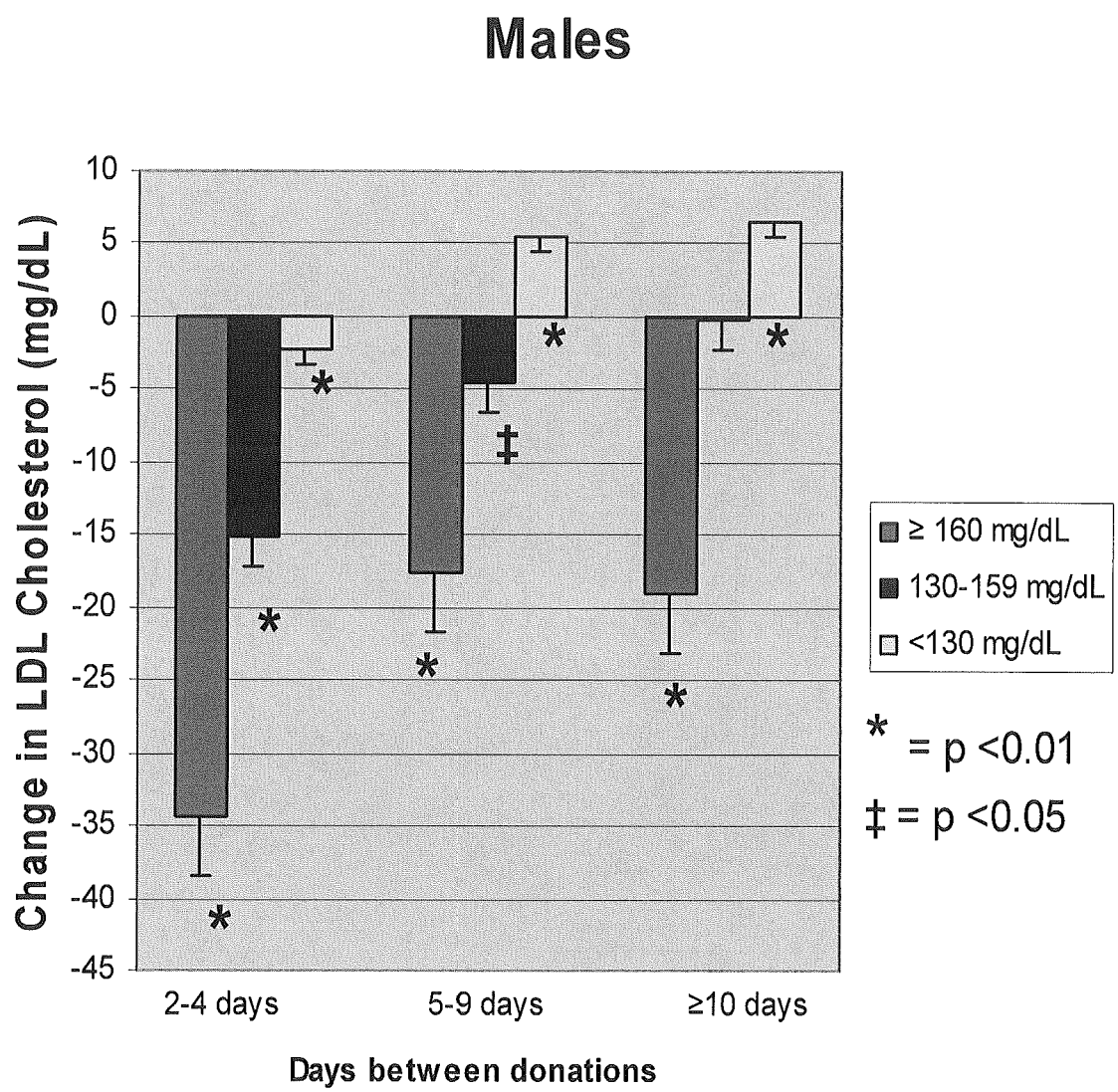
FIG. 8 is a graph illustrating the change in LDL cholesterol based on the number of days between plasmapheresis treatments for male donors.

FIGS. 7 and 8 illustrate the effect of plasmapheresis on LDL levels in male and female donors.

As shown in FIG. 7, female donors having abnormal LDL levels experienced a reduction in LDL levels ranging from about 5 mg/dL to about 40 mg/dL over the course of the study. Female donors undergoing plasmapheresis after 2 to 4 days from the last plasmapheresis and having abnormal LDL levels experienced reductions ranging from about 15 mg/dL to about 40 mg/dL while those undergoing plasmapheresis after 5 to 9 days from the last plasmapheresis experienced reductions of about 10 mg/dL to about 25 mg/dL and those undergoing plasmapheresis after 10 or more days from the previous plasmapheresis saw a reduction of about 5 mg/dL to about 30 mg/dL. It is of note that patients having the highest LDL levels (i.e., greater than about 160 mg/dL) experienced greater losses when treatments were spaced about 2 to about 4 days apart or greater than about 10 days apart than those being in which the rounds were spaced about 5 to about 9 days apart.

As shown in FIG. 8, male donors having abnormal LDL levels (i.e., 130 mg/dL and above) experienced a reduction in LDL levels ranging from about 0 mg/dL to about 35 mg/dL over the course of the study. Male donors undergoing plasmapheresis after 2 to 4 days from the last plasmapheresis and having abnormal LDL levels experienced reductions ranging from about 15 mg/dL to about 40 mg/dL while those undergoing plasmapheresis after 5 to 9 days from the last plasmapheresis experienced reductions of about 10 mg/dL to about 25 mg/dL and those undergoing plasmapheresis after 10 or more days from the last plasmapheresis saw a reduction of about 0 mg/dL to about 20 mg/dL. It is of note that male patients having the highest LDL levels (i.e., greater than about 160 mg/dL) experienced greater losses when treatments were 2 to about 4 days after the previous plasmapheresis or greater than about 10 days after the previous plasmapheresis than those being in which the rounds were spaced about 5 to about 9 days apart. However, male patients having borderline LDL levels ranging from about 130 mg/dL to about 150 mg/dL experienced negligible reduction in LDL levels when rounds of plasmapheresis were spaced more than 10 days apart.

Figure 9:
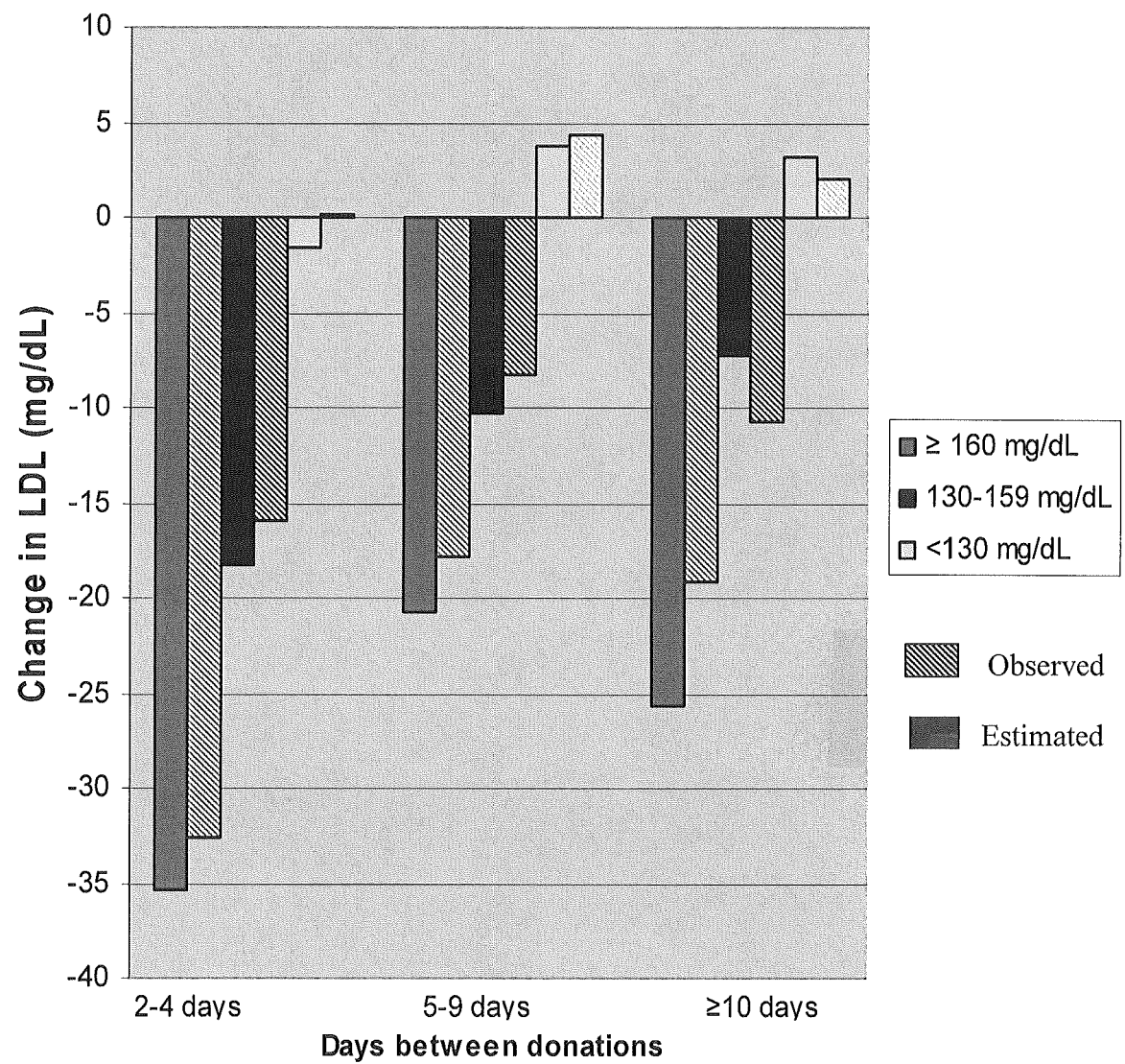
FIG. 9 is a graph comparing the observed and GEE model estimates of the change in LDL cholesterol from baseline for female donors.
Figure 10:
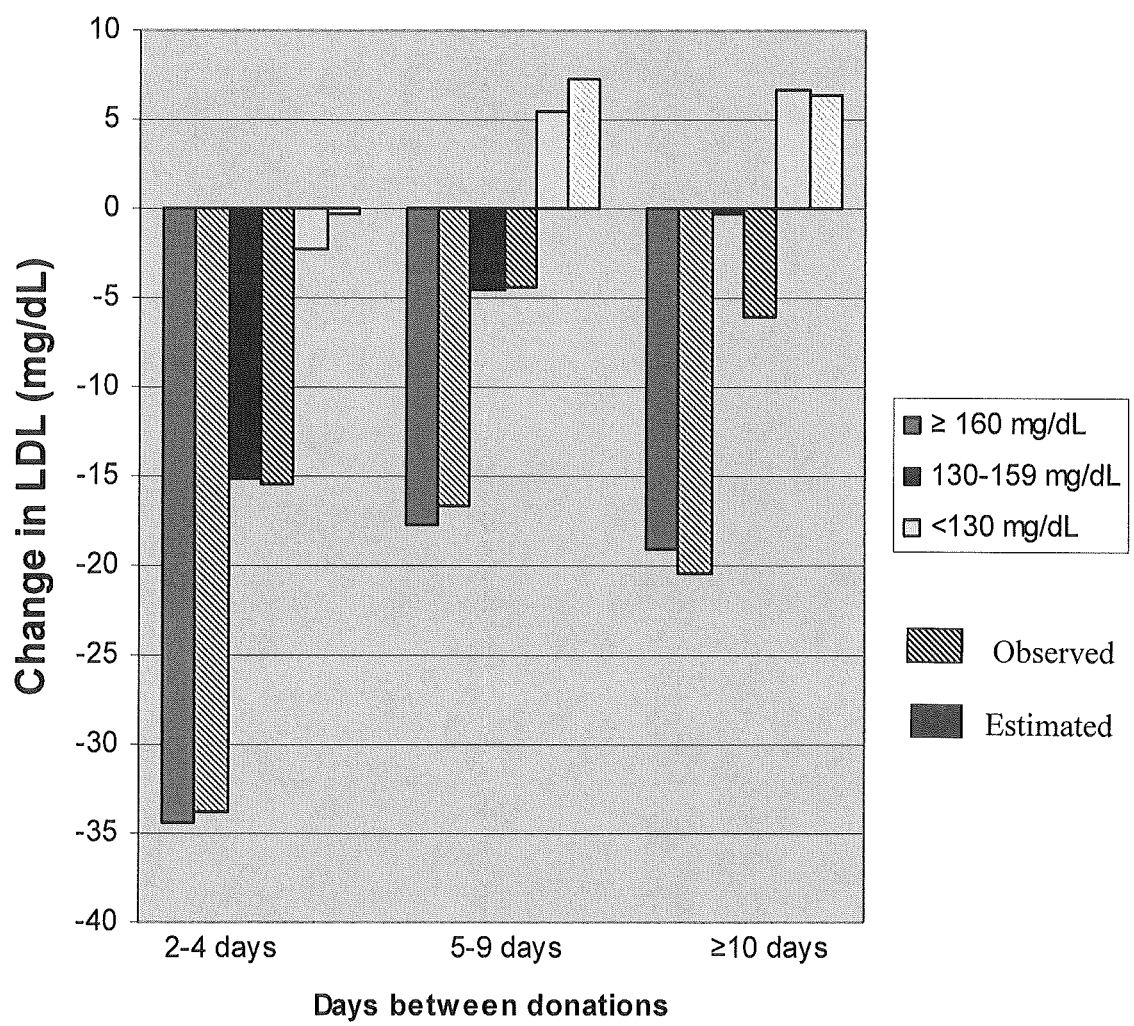
FIG. 10 is a graph comparing the observed and GEE model estimates of the change in LDL cholesterol from baseline for male donors.

FIGS. 9 and 10 illustrate the change from baseline in LDL levels and compare study observations with GEE Model estimates. As shown in FIG. 9, females having high LDL levels (i.e., greater than 160 mg/dL) experienced reductions that were less than those that were estimated. Females having borderline total cholesterol levels (i.e., about 130 mg/dL to about 159 mg/dL) experienced reductions less than those estimated by the GEE model except where greater than 10 days passed between rounds of plasmapheresis.

As shown in FIG. 10, males having high total cholesterol levels (i.e., greater than 160 mg/dL) experienced reductions that were slightly less than those that were estimated for all periods except where greater than 10 days passed between rounds. Males having borderline total cholesterol levels (i.e., about 130 mg/dL to about 159 mg/dL) experienced cholesterol levels that were substantially the same as those estimated by the GEE model except where greater than 10 days passed between rounds of plasmapheresis.

As shown, male and female plasmapheresis donors, who had a high, or higher than desirable baseline total cholesterol levels (i.e., greater than about 200 mg/dL) and LDL levels (i.e., greater than about 130 mg/dL), had an estimated, statistically significant, decrease in cholesterol when plasmapheresis was conducted after 2 to 4 days from the previous one. This predicted change was larger in female donors. The predicted decrease in total cholesterol and LDL levels was smaller in donors with longer intervals between donations, which suggests that there is no long-term effect after discontinuing plasma donation. Moreover, donors with an acceptable baseline total cholesterol (i.e., less than about 200 mg/dL) and LDL (less than about 130 mg/dL) had a very small estimated change or a change that was not statistically significant. In addition, the GEE model estimated results closely paralleled study observed results.

Figure 11:
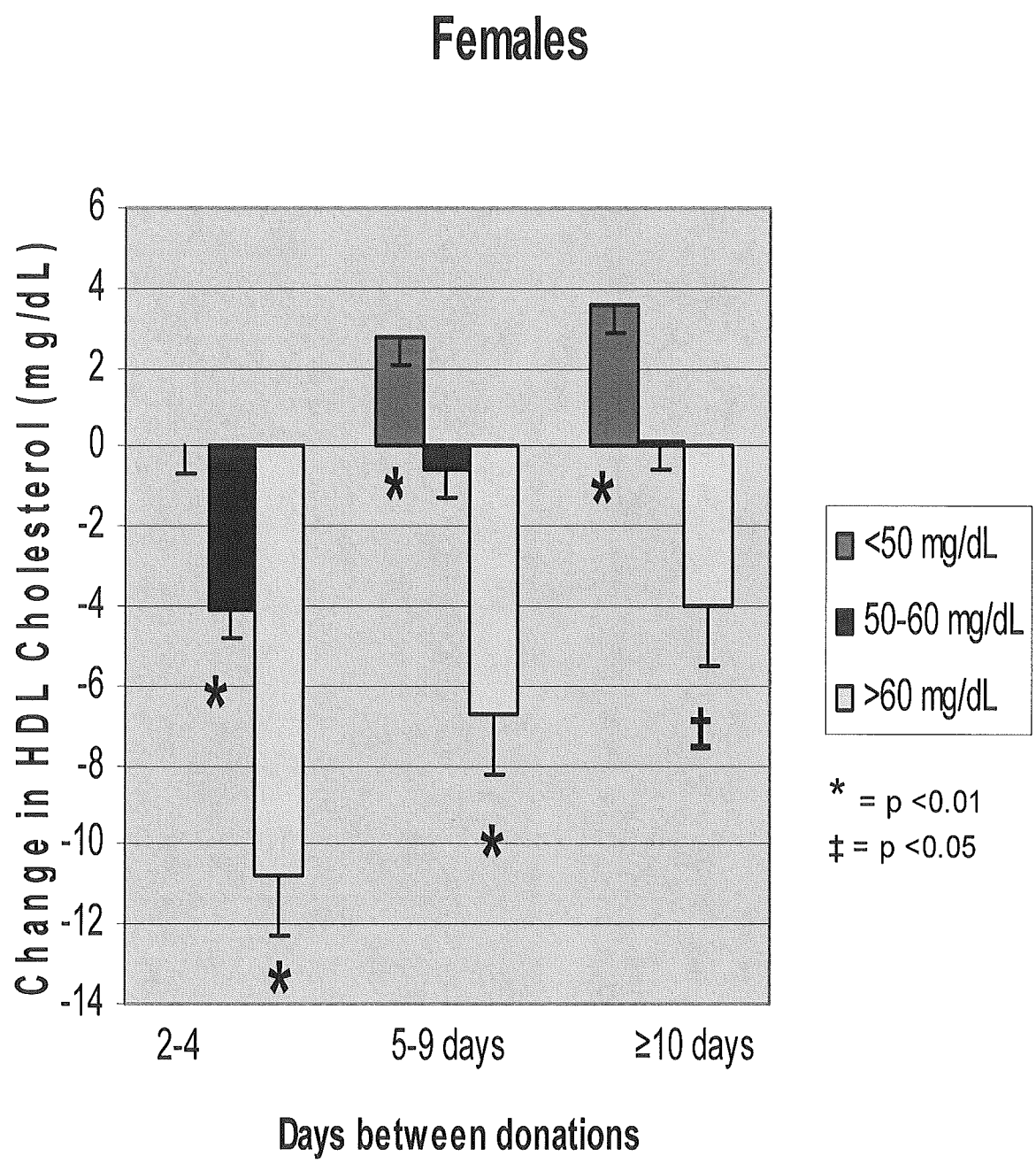
FIG. 11 is a graph illustrating the change in HDL cholesterol for female donors based on the number of days between plasmapheresis treatments.
Figure 12:
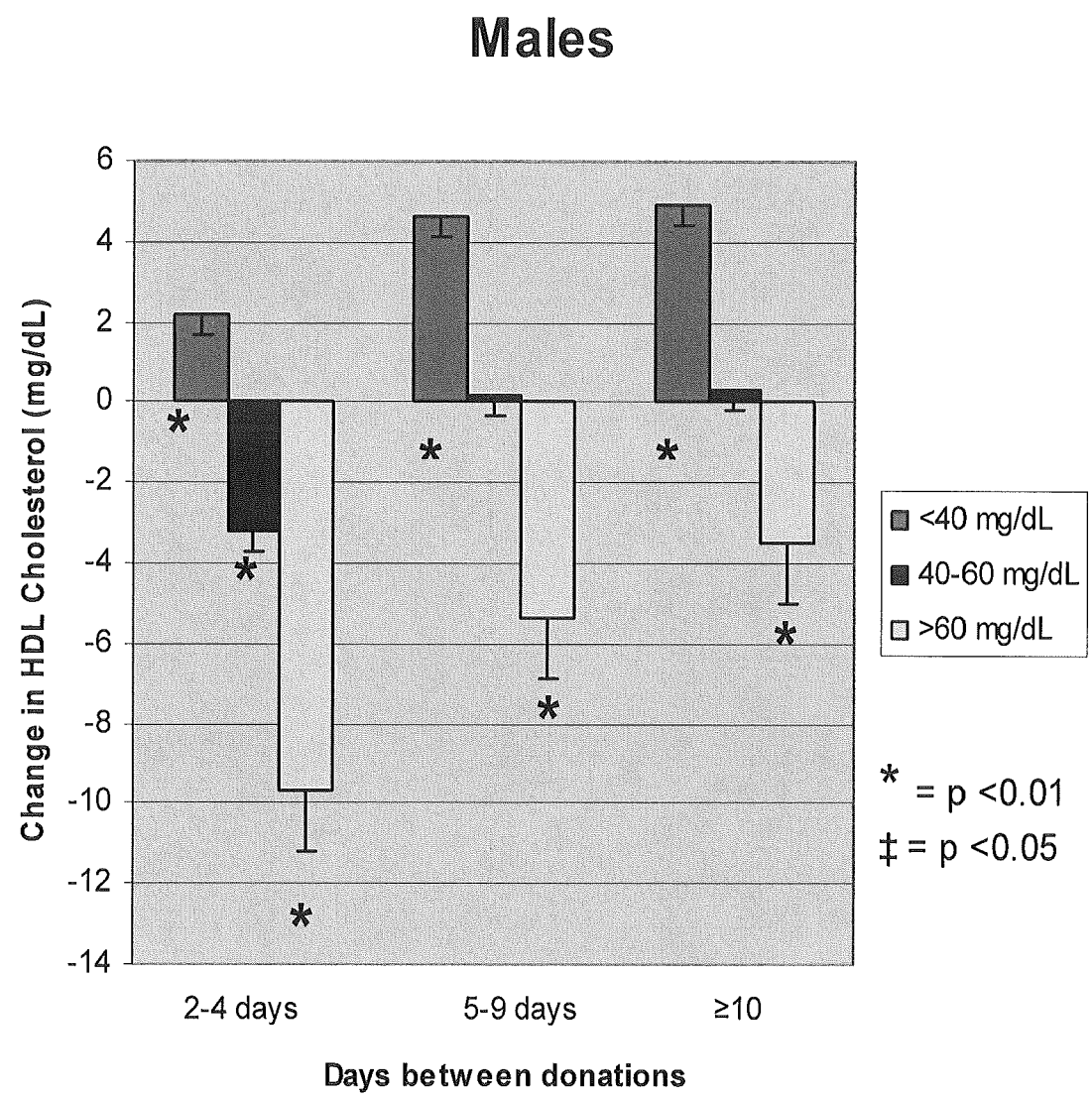
FIG. 12 is a graph illustrating the change in HDL cholesterol based on the number of days between plasmapheresis treatments for male donors.

FIGS. 11 and 12 illustrate the effect of plasmapheresis on HDL levels in male and female donors.

As shown in FIG. 11, female donors having borderline HDL levels (i.e., levels of about 50 mg/dL to about 60 mg/dL) experienced a reduction in HDL levels ranging from about 0 mg/dL to about 5 mg/dL over the course of the study. Those donors having low HDL levels (i.e., less than 50 mg/dL) experienced gains in HDL of about 2 mg/dL to about 4 mg/dL when treatments were done 5-9 days after the last plasmapheresis or greater than 10 days from the previous plasmapheresis. Moreover, any losses observed in patients having normal HDL levels (i.e., greater than about 60 mg/dL) were such that the patients still maintained normal HDL levels after treatment.

As shown in FIG. 12, male donors having abnormal HDL levels experienced a reduction in HDL levels ranging from about 0 mg/dL to about 4 mg/dL over the course of the study, and those having low HDL (i.e., less than about 40 mg/dL) or borderline HDL levels (i.e., about 40 to about 60 mg/dL) experienced gains in HDL of about 1 mg/dL to about 5 mg/dL. Moreover, any losses observed in patients having normal HDL levels (i.e., greater than about 60 mg/dL) were such that the patients still maintained normal HDL levels after treatment.

Figure 13:
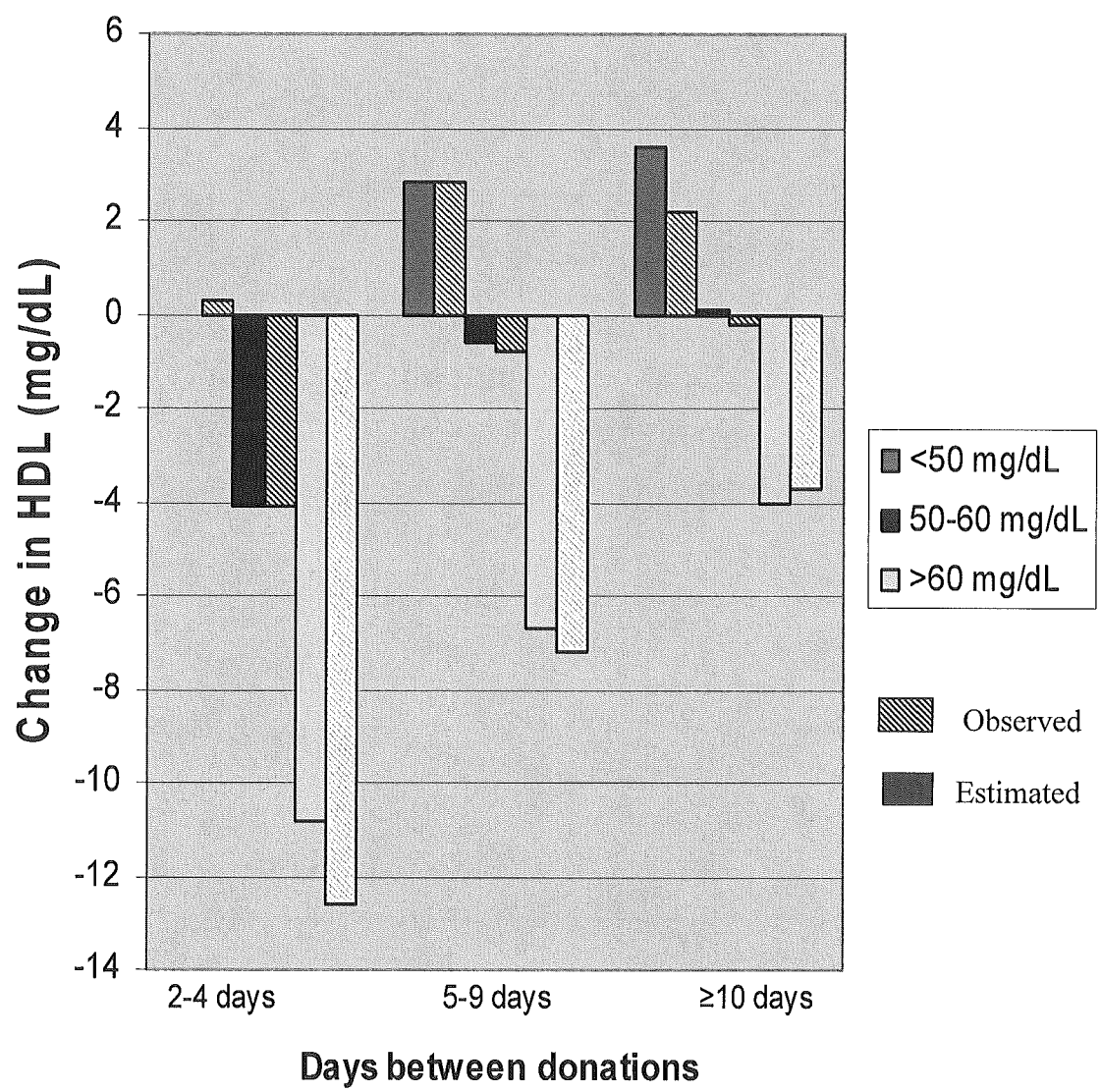
FIG. 13 is a graph comparing the observed and GEE model estimates of the change in HDL cholesterol from baseline for female donors.
Figure 14:
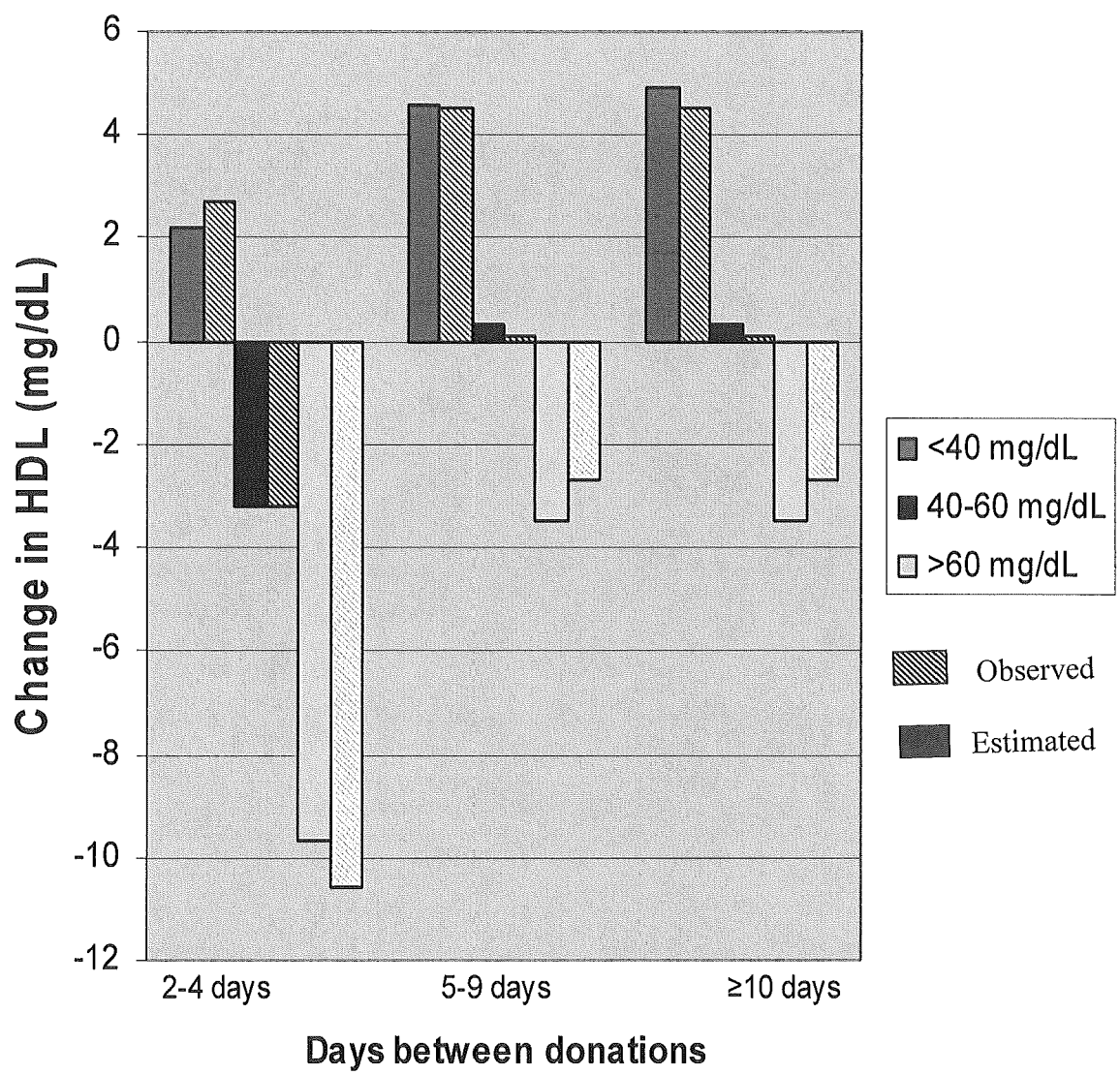
FIG. 14 is a graph comparing the observed and GEE model estimates of the change in HDL cholesterol from baseline for male donors.

FIGS. 13 and 14 illustrate the change from baseline in HDL levels and compare study observations with GEE Model estimates. As shown the GEE model estimated results closely paralleled study observed results.

Donors with a low baseline HDL (i.e., females having baselines of less than 50 mg/dL and males having baselines of less than 40 mg/dL), had an estimated, statistically significant increase in HDL levels. This predicted change was larger with longer donation intervals. Moreover, donors with a near optimal, or optimal HDL levels, had an estimated, statistically significant decrease in HDL levels. This predicted change was smaller with longer donation intervals.

Routine donor monitoring included: blood pressure, pulse, temperature, weight measurement and monitoring of any changes, hematocrit, total protein, and testing for infectious diseases. The results of the study indicated that there was no direct correlation to the total number of donations and the number of deferrals for a given individual.

Adverse symptoms were only reported in 0.15% of the donations. Only 14 donors experienced any adverse effects. No severe symptoms or adverse effects were reported thereby suggesting that the treatment described herein is safe for treatment of blood cholesterol disorders.

The results of this study suggest that the plasmapheresis process affects cholesterol levels in the days following plasmapheresis. The magnitude of the effect observed depends on baseline cholesterol levels and the time between donations.

The recovery of cholesterol levels towards baseline in donors with long intervals between donations suggests that there are no long-term effects after discontinuing plasma donation. Thus, the method described herein is intended for long-term and/or intermittent therapeutic use in treating patients suffering from various cholesterol disorders.

In this specification, the word "about" is often used in connection with numerical values to indicate that mathematical precision of such values is not intended. Accordingly, it is intended that where "about" is used with a numerical value, a tolerance of plus or minus 10% is contemplated for that numerical value.

While the foregoing describes in detail a method of treating cholesterol disorders with reference to a specific embodiment thereof, it will be apparent to one skilled in the art that various changes and modifications and equivalents to the method may be employed, which do not materially depart from the spirit and scope of the invention.

We claim:

1. A method for reducing the level of low density lipoprotein (LDL) in a patient having an LDL level greater than 130 mg/dL, comprising:

identifying a patient having an LDL level greater than 130 mg/dL;

administering to the patient a treatment regime comprising a first round of plasmapheresis and one or more subsequent rounds of plasmapheresis, wherein less than 1000 mL of blood from the patient is treated in each round of plasmapheresis, wherein each round of plasmapheresis separates the blood from the patient into a plasma component and blood cellular components and returns the blood cellular components to the patient without the plasma component, and wherein each subsequent round of plasmapheresis is conducted at least two days after a previous round of plasmapheresis; and monitoring the patient for a reduction in LDL level following the one or more rounds of plasmapheresis.

2. The method of claim 1, wherein each of the one or more subsequent rounds of plasmapheresis is conducted 2-4 days after a previous round of plasmapheresis.

3. The method of claim 1, wherein each of the one or more subsequent rounds of plasmapheresis is conducted 5-9 days after a previous round of plasmapheresis.

4. The method of claim 1, wherein each of the one or more subsequent rounds of plasmapheresis is conducted 10-14 days after a previous round of plasmapheresis.

5. The method of claim 1, wherein the LDL level in the patient is reduced by 10-35 mg/dL.

6. The method of claim 1, wherein the treatment regime lasts for 2 weeks or more.

7. The method of claim 1, further comprising tailoring the treatment regime based on the level of total cholesterol, LDL or HDL in the patient.

8. The method of claim 1, wherein each of the first round and the one or more subsequent rounds of plasmapheresis is effected using a device comprising:
    (a) a housing,
    (b) an entrance port for receiving the whole blood from the patient,
    (c) a centrifuge or a filter for separating the plasma component from the blood cellular components of the whole blood, and
    (d) a catheter for returning the blood cellular components to the patient without the plasma component.

9. The method of claim 1, further comprising administering at least one statin to the patient.

10. The method of claim 1, further comprising administering one or more subsequent treatment regimes to the patient, wherein each of the one or more subsequent treatment regimes comprise two or more rounds of plasmapheresis.

11. A method for increasing the level of high density lipoprotein (HDL) in a patient having an HDL level less than 60 mg/dL, comprising:

identifying a patient having an HDL level less than 60 mg/dL and either abnormal total cholesterol, abnormal LDL levels, or abnormal HDL levels; and administering to the patient a treatment regime comprising a first round of plasmapheresis and one or more subsequent rounds of plasmapheresis, wherein less than 1000 mL of blood from the patient is treated in each round of plasmapheresis, and wherein each round of plasmapheresis separates the blood from the patient into a plasma component and blood cellular components and returns the blood cellular components to the patient without the plasma component.

12. The method of claim 11, wherein each of the one or more subsequent rounds of plasmapheresis is conducted 2-4 days after a previous round of plasmapheresis.

13. The method of claim 11, wherein each of the one or more subsequent rounds of plasmapheresis is conducted 5-9 days after a previous round of plasmapheresis.

14. The method of claim 11, wherein each of the one or more subsequent rounds of plasmapheresis is conducted 10-14 days after a previous round of plasmapheresis.

15. The method of claim 11, wherein the HDL level in the patient is increased by 2-4 mg/dL.

16. The method of claim 11, wherein the treatment regime lasts for 2 weeks or more.

17. The method of claim 11, further comprising tailoring the treatment regime based on the level of total cholesterol, LDL or HDL in the patient.

18. The method of claim 11, wherein each of the first round and the one or more subsequent rounds of plasmapheresis is effected using a device comprising:
   (a) a housing,
   (b) an entrance port for receiving the whole blood from the patient,
   (c) a centrifuge or a filter for separating the plasma component from the blood cellular components of the whole blood, and
   (d) a catheter for returning the blood cellular components to the patient without the plasma component.

19. The method of claim 11, further comprising administering at least one statin to the patient.

20. The method of claim 11, further comprising administering one or more subsequent treatment regimes to the patient, wherein each of the one or more subsequent treatment regimes comprise two or more rounds of plasmapheresis.

* * * * *